US00PP16849P2

(12) United States Plant Patent
Kordes

(10) Patent No.: US PP16,849 P2
(45) Date of Patent: Jul. 18, 2006

(54) MINIATURE ROSE PLANT NAMED 'KORTUFEE'

(50) Latin Name: *Rosa hybrida*
Varietal Denomination: KORtufee

(75) Inventor: Tim-Hermann Kordes, Offenseth-Sparrieshoop (DE)

(73) Assignee: W. Kordes' Söhne Rosenschulen GmbH & Co KG, Sparrieshoop (DE)

( * ) Notice: Subject to any disclaimer, the term of this patent is extended or adjusted under 35 U.S.C. 154(b) by 0 days.

(21) Appl. No.: 11/071,753

(22) Filed: Mar. 2, 2005

(51) Int. Cl.
*A01H 5/00* (2006.01)

(52) U.S. Cl. ..... Plt./121
(58) Field of Classification Search ..... Plt./121
See application file for complete search history.

(56) References Cited

PUBLICATIONS

W. Cord roses, garden roses, master roses, cut roses—your rose world, Contact (translation) [online], [retrieved on Oct. 20, 2005]. Retrieved from the Internet <www.kordes–rosen.com/> one page only.*

III Concurs Internacional de Roses Noves de Barcelona, Barcelona Verda, No. 87, Apr. 2003 [online], [retrieved on Oct. 20, 2005]. Retrieved from the Internet <http://www.b-cn.es/parcsijardins/cat/publicacions/bcnverda/BCN-VERDA_87.pdf>, 5 pages.*

German PBR Application RO82452 Apr. 5, 2004 W. Kordes Söhne.

QZ (CPVO) Application 2004/1559 Aug. 19, 2004 W. Kordes Söhne.

Copy of the cover page(one(1) page) of Kordes Fall 2004/Spring05 Catalog.

Copy of p. 81 (one (1) page) of the W. Kordes Sohne Fall 2004/Spring05 Catalog.

* cited by examiner

*Primary Examiner*—Kent Bell
*Assistant Examiner*—June Hwu

(57) ABSTRACT

A new and distinct variety of rose with long lasting, novel dark pink flowers, and attractive foliage with very good disease resistance. It exhibits compact and uniform growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORtufee'.

BACKGROUND OF THE INVENTION

The new variety of rose plant of the present invention originated from a controlled crossing in a breeding program of two distinct parents during the summer of 1992. The crossing was between 'The Fairy', a non-patented rose and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORtufee'.

SUMMARY OF THE INVENTION

The new rose plant may be distinguished from its seed parent, 'The Fairy' by the following combination of characteristics:

1. 'KORtufee' has deep pink flowers while the seed parent has light pink flowers, and
2. 'KORtufee' has better disease resistance.

The new rose plant may be distinguished from its pollen parent, an un-named seedling by the following combination of characteristics:

1. The applicant has smaller flowers with more petals than the parent variety,
2. The applicant has less vigorous growth than the parent variety.

The objective of the hybridization was to create a new and distinct rose plant with unique qualities, such as:

1. Compact and uniform growth and flowering on plants propagated from both cuttings and grafting;
2. Abundant attractive, recurrent flowers;
3. Attractive and abundant foliage, and;
3. Resistance to diseases encountered in landscapes and gardens.

This combination of qualities is not present in prior rose cultivars. These objectives have been substantially achieved and in that distinguish 'KORtufee' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORtufee' was selected in May, 1993 from the seedling beds to be asexually propagated for further evaluation. The first asexual propagation of 'KORtufee' was done by budding to seedling understocks in July, 1993 at the W. Kordes Söhne Nursery in Offenseth-Sparrieshoop, Germany.

This initial and other subsequent propagations conducted in controlled environments show that the foregoing and all other characteristics of 'KORtufee' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORtufee'. Specifically illustrated in SHEET ONE are flowers and foliage on a plant in bloom.

DETAILED BOTANICAL DESCRIPTION

The following is a description of 'KORtufee', as observed in its growth in summer 2004 on plants of 2 years of age in a field nursery in Sparrieshoop, Germany on plants of 1 year of age. Color references are made using The Royal Horticultural Society (London, England) Colour Chart, 2001 except where common terms of color are used.

For a comparison, several physical characteristics of the rose variety 'The Fairy', a non-patented rose variety are compared to 'KORtufee' in Chart 1.

CHART 1

| Characteristic | 'KORtufee' | 'The Fairy' |
|---|---|---|
| Flower color | Red-Purple Group 67 A. | Red Group 37 C. |
| Flower petals. | Very double. | Double. |

Parents:

*Seed parent.*—'The Fairy'.

*Pollen parent.*—'Un-named seedling'.

Classification:

*Botanical classification.*—*Rosa hybrida*, 'KORtufee'.

*Commercial classification.*—Miniature rose.

FLOWER AND FLOWER BUD

Blooming habit: Recurrent.

Flower bud:

*Size.*—Upon Upening, 12–15 mm in length from base of receptacle to end of bud.

*Bud form.*—Pointed ovoid.

*Bud color.*—As sepals first unfold, bud color is Red-Purple Group 71C. When ¼ open, the upper surface of petals is Red-Purple Group 67B, and the lower surface is Red-Purple Group 67A.

*Sepals.*—Size: Average 25–30 mm long×8–10 mm wide. Shape: Moderate foliaceous appendages on three of the five sepals. Sepal apex is cirrose. Base is flat at union with receptacle. Quantity: Five. Surface texture: Upper and lower surfaces covered in fine hairs. Stipitate glands on margins of the sepals. Color: Upper surface Green Group 138A. Lower surface Green Group 138A.

Receptacle:

*Surface.*—Smooth.

*Color.*—Green Group 138A.

*Shape.*—Funnel.

*Size.*—6–7 mm (h)×8–10 mm (w).

Peduncle:

*Surface.*—Smooth to lightly pubescent.

*Length.*—30–50 mm average length.

*Diameter.*—2–3 mm average diameter.

*Color.*—Green Group 138A.

*Strength.*—Strong.

*Borne.*—Multiple flower buds per stem, generally 15 to 25.

Flower bloom:

*Fragrance.*—Light fresh scent.

*Duration.*—On the plant 4–6 days. Senesced petals drop away cleanly.

*Size.*—Small flowered garden rose. Average flower diameter is 25–35 mm when open.

*Form.*—Shape of flower when viewed from the side: Upon opening, upper part: Flattened convex. Upon opening, lower part: Flat. Open flower, upper part: Flattened convex. Open flower, lower part: Flat.

Color:

*Upon opening, petals.*—Outermost petals: Outer Side: Red-Purple Group 67A. Inner Side: Red-Purple Group 67B. Innermost petals: Outer Side: Red-Purple Group 67A. Inner Side: Red-Purple Group 67B.

*Upon opening, basal petal spots.*—Basal petal spot, outermost petals: Outer Side: White Group 155C. Inner Side: White Group 155C. Basal petal spot, innermost petals: Outer Side: White Group 155C. Inner Side: White Group 155C.

*After opening, petals.*—Outermost petals: Outer Side: Red-Purple Group 67B. Inner Side: Red-Purple Group 67C. Innermost petals: Outer Side: Red-Purple Group 67A. Inner Side: Red-Purple Group 67B.

*After opening, basal petal spots.*—Basal petal spot, outermost petals: Basal petal spot, outermost petals: Outer Side: White Group 155C. Inner Side: White Group 155C. Basal petal spot, innermost petals: Outer Side: White Group 155C. Inner Side: White Group 155C. Variegations: Occasional white streak on the guard petals.

General tonality: On open flower Red-Purple Group 67B No change in the general tonality at the end of the $4^{th}$ day. Afterwards, general tonality is Red-Purple Group 67C.

Petals:

*Petal count.*—Approximately 45–55 petals under normal conditions.

*Petal reflex.*—Petals reflex slightly.

*Petal edge.*—Entire.

*Petal shape.*—Apex shape is deltoid. Shape of base is acute.

*Petal size.*—15 mm long; 10 mm wide.

*Thickness.*—Average.

*Petal arrangement.*—Generally in a regular pattern with overlapping edges.

*Petaloids.*—Average of 8–10 per flower. Shape: Linear. Average size: 8 mm in length and 2–3 mm in width. Color of the outer side is Red-Purple Group 67A. Color of the inner side is Red-Purple Group 67B.

Reproductive organs:

*Pistils.*—Approximately 30. Stigmas: Location: Slightly inferior in location to anthers. Color: Yellow Group 1D. Styles: Length: 5 mm long. Color: Yellow-Green Group 150D.

*Stamens.*—Quantity: Approximately 30. Anthers: Size: 6–8 mm long. Color: Yellow-Green Group 150D. Pollen: Generally present.//Absent. Color: Greyed-Orange Group 174D. Filaments: Color: Yellow-Green Group 150D. Length: 6–8 mm.

THE PLANT

Plant growth: Moderate vigor. Compact habit. When grown as a budded nursery plant the average plant height is 50 cm and the average plant width is 40 cm.

Stems:

*Stem color.*—Young wood: Green Group 138A. Older wood: Green Group 138A.

*Stem surface.*—Young wood: Smooth. Older wood: Smooth.

Prickles:

*Incidence.*—Few. 2 per 10 cm of stem.

*Size.*—Average length: 4 mm.

*Color.*—Immature and mature prickles Greyed-Red Group 181D. Senescing to Grey-Brown 199C.

*Shape.*—Linear.

Leaves and leaflets: Normally 5 leaflets on normal leaves in middle of the stem.

*Leaf size.*—80–85 mm (l)×55 mm (w). Average size of the terminal leaflet is 30 mm (l)×22 mm (w).

*Shape.*—Pointed oval. Basal shape obtuse. Apex shape is narrowly acute.

*Quantity.*—Average abundance.

*Texture.*—Matte to slightly glossy. Smooth.

*Color, mature foliage.*—Upper Leaf Surface: Green Group 137A. Lower Leaf Surface: Green Group 137A.

*Color, juvenile foliage.*—Upper Leaf Surface: Green Group 137A. Lower Leaf Surface: Green Group 137A.

*Anthocyanin intonations.*—Present. Greyed-Purple Group 183C on juvenile leaves, leaflets, petiole, rachis, prickles, and stipules.

Stipules:

*Size.*—15–17 mm (l)×6–8 mm (w).

*Stipule color.*—Green Group 137A.

*Presence of stipitate glands.*—Present on margins.

*Margins.*—Bearded.

Petiole: Smooth to lightly pubescent underneath.

*Length.*—10–12 mm.

*Petiole color.*—Green Group 137A.

*Prickles.*—Generally absent.

*Stipitate glands.*—Present.

*Diameter.*—1.5 mm average diameter.

Petiole rachis:

*Color.*—Green Group 137A. Anthocyanin on juvenile petiole rachis more concentrated in margins.

*Prickles.*—Small prickles located on underside.

*Stipitate glands.*—Present. Generally on margins.

Leaflets:

*Shape.*—Elliptic to ovate.

*Margins.*—Finely serrated.

*Texture.*—Leathery.

Hips/seed formation: None observed.

Winter hardiness observation: To date, the new variety has been grown successfully in Zone 5.

Disease resistance: Excellent resistance to black spot, powdery mildew, and rust under normal growing conditions.

I claim:

1. A new and distinct variety of rose plant characterized by the following combination of characteristics:

(a) forms attractive, long lasting dark pink flowers;

(b) exhibits compact and uniform growth habit;

(c) propagates well using traditional methods, and;

(d) exhibits excellent resistance to disease under normal growing conditions;

substantially as herein illustrated and described.

* * * * *

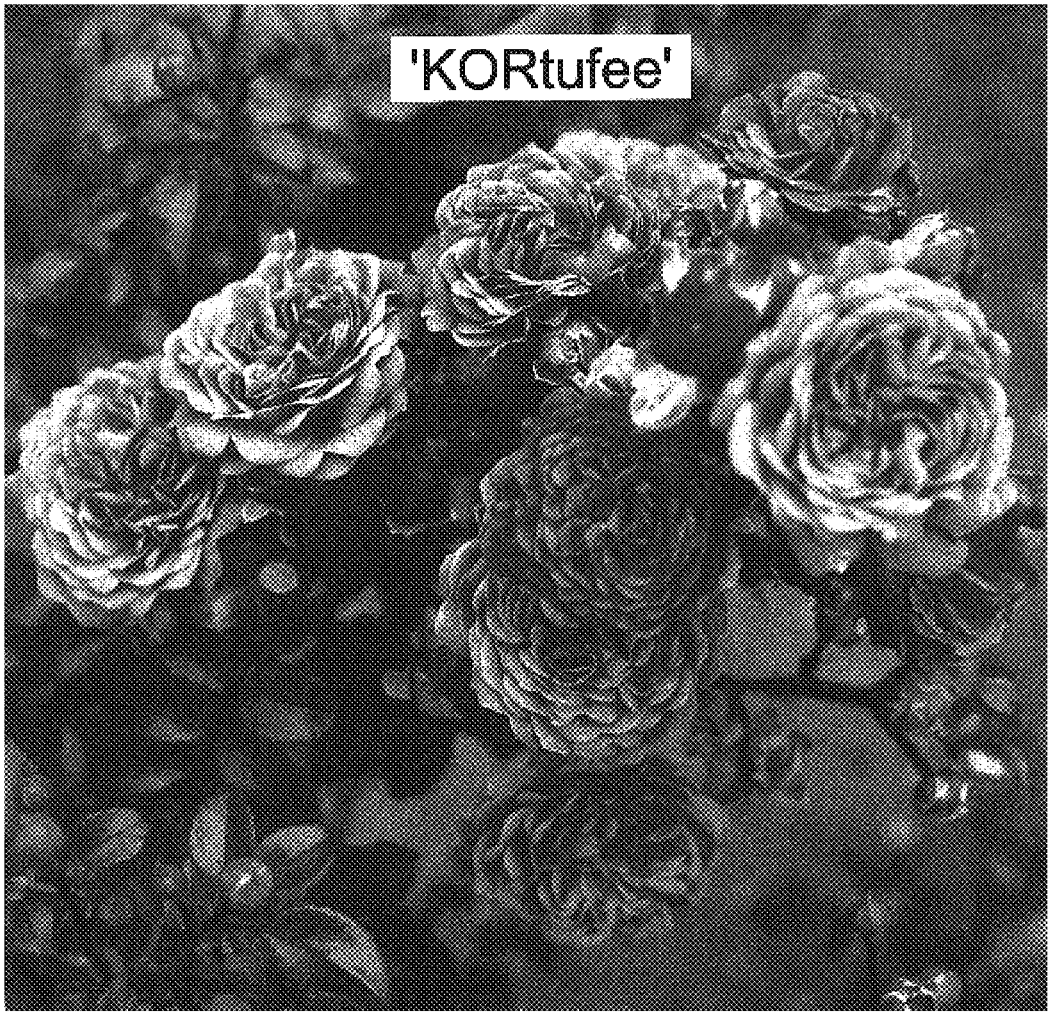
'KORtufee'